United States Patent [19]

Burstone et al.

[11] 4,197,643

[45] Apr. 15, 1980

[54] ORTHODONTIC APPLIANCE OF TITANIUM ALLOY

[75] Inventors: Charles J. Burstone, Farmington; A. Jon Goldberg, West Hartford, both of Conn.

[73] Assignee: University of Connecticut, Farmington, Conn.

[21] Appl. No.: 886,430

[22] Filed: Mar. 14, 1978

[51] Int. Cl.² .................. H01L 7/58; A61C 7/00; C22C 14/00
[52] U.S. Cl. ................. 433/20; 75/175.5; 148/32.5
[58] Field of Search .......... 29/DIG. 45; 32/14; 75/175.5; 148/32.5, 1.33

[56] References Cited

U.S. PATENT DOCUMENTS

| | | | |
|---|---|---|---|
| 2,798,806 | 7/1957 | Jaffe et al. | 75/175.5 |
| 2,798,807 | 7/1957 | Crossley et al. | 75/175.5 |
| 3,052,976 | 9/1962 | Rennhack | 29/DIG. 45 |
| 3,351,463 | 11/1967 | Rozner et al. | 148/120 |
| 3,748,194 | 7/1973 | Ruckle et al. | 148/32.5 |
| 3,767,480 | 10/1973 | Schuler et al. | 148/32.5 |
| 4,037,324 | 7/1977 | Andreasen | 32/14 A |
| 4,055,975 | 11/1977 | Serfozo et al. | 29/DIG. 45 |
| 4,067,734 | 1/1978 | Curtis et al. | 148/32.5 |
| 4,094,708 | 6/1978 | Hubbard et al. | 148/32.5 |
| 4,098,623 | 7/1978 | Ibaraki et al. | 75/175.5 |

OTHER PUBLICATIONS

L. Galton, "An Easier, Quicker Way to Straighten Teeth," Parade Magazine, Jun. 12, 1977.

Primary Examiner—Russell R. Kinsey
Assistant Examiner—Michael J. Foycik, Jr.
Attorney, Agent, or Firm—Prutzman, Kalb, Chilton & Alix

[57] ABSTRACT

A beta-titanium alloy wire is used as the force-imparting component in orthodontic appliances. The alloy provides up to a threefold improvement over 18-8 stainless steel wire in load deflection rate and a twofold increase in maximum elastic displacement while providing a low modulus of elasticity and optimum low level force magnitudes. The wire also finds utility as ligature wires, as clasps and related structures in orthodontic and prosthetic appliances and as surgical arch bars for jaw fractures and the like.

11 Claims, 4 Drawing Figures

U.S. Patent    Apr. 15, 1980    4,197,643
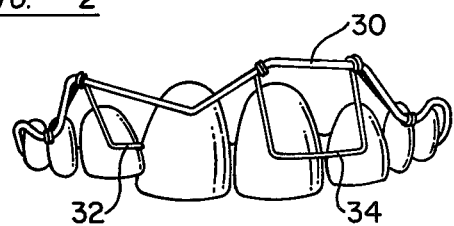
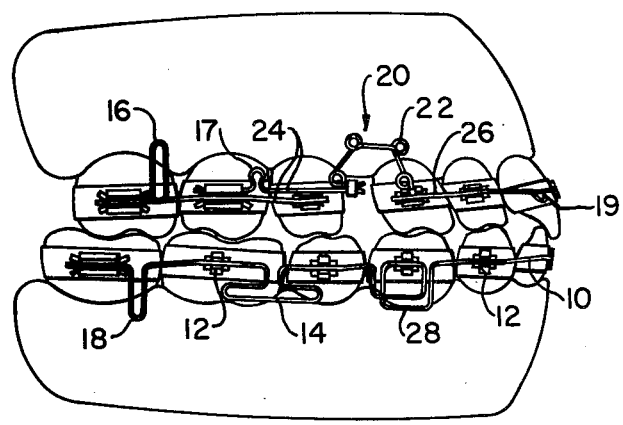
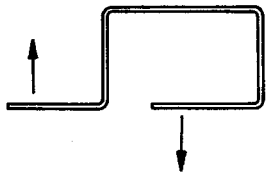
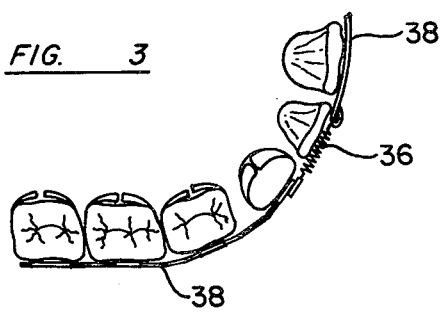

ORTHODONTIC APPLIANCE OF TITANIUM ALLOY

BACKGROUND AND SUMMARY OF THE INVENTION

The present invention relates generally to appliances used in dentistry and is more paticularly concerned with new and improved appliances used principally in orthodontics but also having application to prosthetics and oral surgery.

As is well known, orthodontic appliances are used to manipulate certain teeth to correct irregularities and/or abnormalities in their relationships with surrounding members. This is achieved by using force systems that have their origin primarily in elastically-deformed wires which absorb and release energy during loading and unloading. Heretofore, the force-imparting wires used in orthodontic treatment have been made mainly from 18-8 stainless steel wires that take advantage of the bending and torsional properties of that wire.

As mentioned in the article by C. J. Burstone et al entitled "Force Systems From An Ideal Arch," *American Journal of Orthodontics,* Volume 65, pages 270–289 (1974), proper application of the correct forces requires not only the study of suitably contoured and clinically dimensioned shapes or configurations together with variations in the cross-sectional dimensions of the force-imparting wire, but also a better understanding of the biomechanics involved in orthodontic appliances. Heretofore, efforts have been directed almost exclusively toward the development of optimum appliance configurations with only ancillary consideration being given to the material used for the appliances.

With respect to biomechanics, it was reported by C. J. Burstone et al in *Angle Orthodontist, Volume* 31, pages 1–14 (1961), that desirable tooth movement can best be achieved by producing an optimal force system capable of delivering relatively light but continuous corrective forces. The primary or basic biomechanical characteristics include a lower force magnitude whereby the teeth will move rapidly and relatively painlessly with minimum tissue damage, a constant force level over time as the appliance experiences deactivation in order to provide maximum tissue response, an accurate location of the point of application of the force or its equivalent, a uniformity in the force applied through the total distance over which the force acts. It also is desirable to provide within a orthodontic appliance the ability to undergo large deflections without deformation. Of course, if the force acting on the teeth decays too rapidly, the teeth will move more slowly and it becomes more difficult to accurately produce the desired effect.

Heretofore, the force magnitude applied to the teeth was determined in part by the cross section of the wire used in the appliance, with smaller wires providing the desired lower or reduced force. As will be appreciated, larger wires fit well in the slots of band-mounted or directly bonded brackets or the lumen in a tube and a good fit is necessary for controlled tooth movement. If smaller wires are used, the play between the wire and the bracket leads to loss of control. Reduction in slot or lumen size is undesirable since (1) it is more difficult to control tolerances and (2) manufacturing variations in wire cross section have a proportionately greater effect on force magnitudes. Despite this, a reduction in the wire cross section with its attendant reduction in load deflection rate historically has been the course followed to achieve force constancy using 18-8 stainless steel wire. In this connection, care must be taken since too great a reduction in cross section can result in permanent deformation before optimal forces are reached.

Although the principal and predominant emphasis in orthodontic research has been on improved appliance design, and relatively little attention has been given to alternatives for the conventionally employed 18-8 stainless steel wire, efforts are now being made in providing the aforementioned desirable biomechanical characteristics through the use of alternative materials. One example of such an approach can be found in the proposed utilization of Nitinol alloys of the type described in U.S. Pat. No. 3,351,463. These materials are near-stoichiometric intermetallic compounds of nickel and titanium, preferably having cobalt substituted for the nickel on an atom to atom basis. The alloy can be preformed below its critical transition temperature and, when heated to above that temperature, will display a mechanical memory causing the material to return to its predisposed shape. The application of this material to orthodontics is set forth in U.S. Pat. No. 4,037,324 where the longitudinal shrinkage characteristic of the wire is used. Although this intermetallic material is reported to be quite ductile, it has been found in practice that the material will not withstand cold bending into major orthodontic configurations and cannot be used for closing loops and the like. This, of course, severly limits the alloy's use in the formation of appliances that require significant bends in their design. Additionally, the material cannot be welded or soldered, thereby substantially hampering its utilization.

The present invention solves many of the problems encountered heretofore when using stainless steel or Nitinol while, at the same time, facilitating the delivery of optimum orthodontic forces. Accordingly, it is an object of the present invention to provide a new and improved orthodontic appliance utilizing an orthodontic force-imparting wire that provides optimum orthodontic force characteristics including the preferred low force magnitude and force constancy over a prolonged period of time to achieve continuous, relatively painless tooth movement with maximum tissue response and minimum tissue damage. Included in this object is the provision for a force-imparting wire exhibiting a low modulus of elasticity relative to the 18-8 stainless steel wires used heretofore.

Another object of the present invention is to provide a new and improved orthodontic appliance of the type described that facilitates the application of a given force with greater ease and accuracy and exhibits the ability to undergo larger deflections without deformation, therefore providing an associated increase in the effective working time of the appliance while meeting the necessary criteria of biocompatability, formability and environmental stability.

Yet another object of the present invention is to provide an orthodontic appliance of the type described that utilizes a new and improved force-imparting wire exhibiting a lower modulus of elasticity, a greater maximum elastic deflection and a greater ratio of yield strength to modulus of elasticity while reducing the need for periodic installation of wires of reduced cross section. Included in this object is the provision for the use of a wire of moderate cross section, thereby minimizing the need for closer wire tolerances for achieving desired first order deflections. Also included is the provision for wires whose force magnitudes and moment to force ratios are controlled by selection of the modulus of elasticity rather than the traditional approach of simply modifying the cross section.

Still another object of the present invention is to provide a new and improved orthodontic appliance of the type described that utilizes room temperature stabilized beta-titanium alloys capable of being formed into a wide array of orthodontic appliances from the simple to the highly complex orthodontic configurations in order to deliver the optimum moment to force ratios such that the appliance acts on the crown of the tooth to provide the accurate center of rotation of the tooth as it is moved. Included in this object is the provision for the use of a stabilized beta-titanium material capable of taking advantage of the excellent plasticity and formability characteristics associated with its beta crystalline structure yet, at the same time, providing the desired strength characteristics by controlling the mechanical and thermal history of the solid solution alloy.

A still further object of the present invention is to provide a new and improved orthodontic appliance of the type described which exhibits the ability to be welded to base or main arches or segments thereof without materially affecting the mechanical properties of the appliance. For example, hooks, tiebacks, ligature wires and springs made from the beta-titanium alloy wire can be directly welded, unlike the 18-8 stainless steel that requires an elaborate and time consuming soldering process which negatively influences wire properties such as yield strength. The weldability of the material also facilitates greater flexibility of use wherein lighter control wires can be rigidly secured to the heavier wires to assure proper anchorage for the delivery of optimum magnitude forces at more constant force rates.

Other objects will be in part obvious and in part pointed out more in detail hereinafter.

These and related objects are achieved in accordance with the present invention by providing an orthodontic appliance that utilizes a force-imparting wire formed from a room temperature stabilized beta-titanium alloy having a modulus of elasticity well below $20 \times 10^6$ psi. The titanium alloy wire provides a ratio of yield strength to modulus of elasticity up to 80% greater and more than that of 18-8 stainless steel wire of the same cross section and exhibits a higher maximum elastic deflection than such stainless steel wire. The titanium alloy wire further is characterized by an ability to provide a lower and more constant force component over a longer period, thereby enhancing the effective working time of the appliance and by an ability to withstand repeated cold bending into major orthodontic configurations.

A better understanding of the invention will be obtained from the following detailed description and the accompanying drawing of illustrative applications of the invention wherein the features, properties and relation of elements are described and exemplified.

BRIEF DESCRIPTION OF THE DRAWING

In the drawing:

FIG. 1 is a side elevational view of an upper and lower jaw illustrating the manner in which various orthodontic devices such as archwires and auxiliary members may be employed, FIG. 2 is a front elevational view of an upper jaw portion with a removable orthodontic appliance mounted thereon, FIG. 3 is a partial plan view of a jaw illustrating a different orthodontic archwire application, and FIG. 4 is a plan view of a rectangular loop spring used in the appliance of the present invention.

DESCRIPTION OF THE PREFERRED EMBODIMENT

Referring now to the drawing in greater detail wherein like reference numerals indicate like parts throughout the several figures, the present invention is illustrated using beta-titanium alloy wires that have been fabricated into various orthodontic appliances capable of delivering one-half and less the force of 18-8 stainless steel with a more constant force and good bracket engagement for controlled tooth movement. The system of the present invention allows the use of relatively large wire cross sections for devices delivering a lower force through the employment of materials exhibiting a low modulus of elasticity. For example, the devices amy employ wires having cross sections in the range of 0.1 mm. to 2.0 mm. In accordance with this system, optimum force magnitudes are more readily and accurately delivered since the wire of larger cross section minimizes the effect of tolerance factors at the attachment between the wire and its mounting, such as the archwire 10, and the tooth-mounted bracket 12 shown in FIG. 1. Additionally, the beta-titanium alloy material permits the use of constant cross sections of wire during treatment, such as ribbon, edgewise or round cross section wires. In this way, force magnitudes are controlled by the alloy itself rather than by varying the cross section of the wire, as has been the traditional practice in the past.

The desired optimum force constancy is produced in accordance with the present invention by reducing the load deflection rate through the use of beta-titanium as the alloy material for the orthodontic wire. Since the beta-titanium alloys permit the optimization of appliance properties by controlling the mechanical and thermal history of the material, and since, as is known, the load deflection rate of wires is a function of the modulus of elasticity of the material, it is possible, in accordance with the present invention, to provide a modulus of elasticity that is approximately two thirds and less than that of stainless steel.

The high formability of such wires facilitates the production of a wide variety of orthodontic devices from the simple to the complex in order to deliver the desired momentum to force ratios. As shown, the appliance may include complex configurations or auxiliary members, such as the T-loop 14, the vertical loops 16, 17, 18 and the attached hook 19. Space closure may be achieved using an anterior retractor assembly of the type shown at 20 on the upper jaw of FIG. 1. Such a device also may combine the use of a complex spring 22 made of the beta-titanium alloy with stainless steel archwire segments 24, 26 to provide the space closure and root movement functions. Additionally, braided wires and ligature wires may be formed from the beta-titanium alloy wires of the present invention due to the high ductility of the material prior to heat aging. Previously, a lower hardness than desired was used for braiding since the cold working during manufacture caused brittleness and fracture in the 18-8 stainless steel material. This formability characteristic of the beta-titanium alloy, coupled with its ability to be hardened following fabrication of the most complex orthodontic configuration, enables the device to accurately operate at the point of attachment to the crown of the tooth and provide the proper and designated center of rotation for the tooth as it is moved during treatment.

The high ductility of the beta-titanium wires can be used to advantage when forming specialized complex springs such as the rectangular spring 28. Additionally, the material is well suited for such applications as cuspid and anterior retraction, as illustrated in FIG. 1, root movement, tooth alignment and leveling. This excellent formability resulting from the high ductility of the material does not detract from the ability of the material to be formed into clasps or retaining devices for orthodontic retainers, prosthetic appliances and removable clasp-like appliances, such as the appliance shown in FIG. 2. The working components of the appliance, such as the labial bow 30, finger spring 32 and apron spring 34, advantageously maintain their shape under patient-induced loads. In addition, lingual arches fabricated of beta-titanium deliver optimum forces more constantly. As will be appreciated, the form taken by the spring may vary widely and only a few representative examples are shown in the drawing by the springs in FIG. 2 and the coil spring 36 secured to the archwire segments 38 in FIG. 3.

Orthodontic appliances using the beta-titanium wires of the present invention also have the advantageous feature of the ability to be welded. Thus, the springs, tiebacks, hooks or other auxiliaries may be welded directly to a heavier wire such as lingual arches, a base arch or other arch wire, thereby eliminating the need to solder such springs in place as is necessary with conventional orthodontic devices. It is significant that the welding of the beta-titanium material does not substantially affect the properties of the material, thus permitting its use for applications such as root and rotation springs and facilitating the welding of one or more wires into a solid configuration in one area for rigidity and anchorage control while permitting freedom of individual strands in other areas for delivery of the lighter optimum force magnitudes.

One of the principal advantages of the beta-titanium alloy system of the present invention is the wide range of properties that can be obtained using this material as a result of the thermal and mechanical treatments to which the material is subjected. Thus, by appropriate selection of the material and its treatment, it is possible to vary the modulus of elasticity of the beta-titanium alloy so that it varies over a wide range well below $20 \times 10^6$ psi. For example, the modulus of elasticity of the beta-titanium alloys may vary over the range of about $6 \times 10^6$ psi to about $18 \times 10^6$ psi with most of the alloys falling within the range of $8-16 \times 10^6$ psi. This is of substantial significance when compared to the relatively non-varying modulus of elasticity exhibited by 18-8 stainless steel orthodontic wires which typically fall within the range of $27-31 \times 10^6$ psi.

Since the maximum elastic deflection of a wire is a function of the ratio of yield strength to modulus of elasticity, it is also important to consider the yield strength of the beta-titanium alloy material. Once again, in accordance with the present invention, this alloy provides for variability in the yield strength between about $7 \times 10^4$ psi and $30 \times 10^4$ psi, the higher values being comparable to those obtained from stainless steel. The yield strength variation is, of course, not completely independent of the changes in modulus of elasticity. Rather, the strength varies therewith such that an increase in yield strength may, but need not necessarily, result in a corresponding increase in the ratio of yield strength to modulus of elasticity. In any event, a substantially higher ratio can be found in the beta-titanium alloys relative to the 18-8 stainless steel and a corresponding increase can be realized in the maximum elastic deflection of that material. Thus, by providing a two to threefold increase in the ratio of yield strength to modulus of elasticity and by reducing the modulus of elasticity by a factor up to about three, lower force magnitudes are delivered more constantly over a larger range of action than in the traditional orthodontic appliance. This optimized higher yield strength and lower modulus of elasticity is achieved while providing excellent weldability and formability even after considerable cold working. The alloy of the present invention also provides good environmental stability and biocompatability with oral tissues.

Since the variability of properties within the betatitanium alloys of the present invention depends to some degree on the specific chemistry and thermal-mechanical history of the material, it is desirable to present a limited explanation of the nature of the beta-titanium alloy materials. In this connection, it is known that unalloyed titanium can exist in two allotropic crystallographic forms. At temperatures up to 1625° F., titanium maintains a hexagonal close-packed crystal form, while at temperatures above 1625° F., the metal atoms occupy a body-centered cubic arrangement. Conventionally, the low temperature form is termed the "alpha" form, while the high temperature form is designated as "beta." Alloying constituents that have a body-centered cubic lattic such as molybdenum, columbium, tantalum and vanadium tend to stabilize the beta-titanium phase and thus cause a lowering of the alpha to beta transformation temperature. Thus, the high temperature beta-titanium can be obtained at room temperature by rapidly cooling an alloy-stabilized beta phase and inhibiting the beta to alpha transition. The material that is sufficiently alloyed with beta-stabilizers so that the body-centered cubic structure is maintained upon cooling to room temperature from the beta field is termed a beta-stabilized titanium alloy or, more simply, a beta-titanium alloy. This material is predominantly titanium and may contain up to about 25% by weight and more of the alloying constituents. The stabilizing alloying elements, in addition to those mentioned, can include manganese, iron, chromium, cobalt, nickel, and copper as well as aluminum, tin and zirconium. Further details with respect to the composition of this type of material can be obtained from the Jaffee et al U.S. Pat. No. 2,797,996 issued July 2, 1957, and entitled "Titanium Base Alloys."

The body-centered cubic structure of the alloy provides a material of excellent plasticity and high ductility, permitting the material to be readily formed and fabricated into the most complex orthodontic configurations. It is also known that these materials possess the potential for very high strength and deep hardenability through either cold working or heat treatment aging. Thus, the alloy-stabilized beta-titanium phase can be transformed to a beta phase containing heat-induced precipitated alpha phase therein to greatly enhance the strength characteristic of the material. Typically, the beta-titanium alloy will be heated to the high temperature or beta form followed by rapid cooling to room temperature to obtain the beta-stabilized room temperature alloy. This beta-stable material in the condition termed solution heat treated or fully annealed is highly ductile and can be formed into the desired orthodontic appliances at this stage or after partial or complete strengthening. This strengthening, coupled with reduced ductility, is achieved by either cold working or by heat treatment aging at elevated temperatures over varying time periods. Thus, the superior ductility and low strength of the body-centered cubic structure make it ideally suited for the production of highly complex structures. This property also permits extensive cold working which, in itself, may impart the required strength characteristics to the final product, thereby eliminating the need for heat aging.

The specific chemistry of commerical beta-titanium alloy materials is known. Typical beta-titanium alloys have the following approximate alloying compositions:

A. 13% vanadium, 11% chromium, and 3% aluminum;
B. 8% molybdenum, 8% vanadium, 2% iron and 3% aluminum;
C. 11.5% molybdenum, 6% zirconium and 4.5% tin; and
D. 3% aluminum, 8% vanadium, 6% chromium, 4% zirconium and 4% molybdenum.

Although the beta-titanium alloys have been studied for aerospace application, most of the work conducted heretofore has centered on maximizing the strength characteristics of the material to optimize strength-to-weight ratios. This prior work has been concerned with material exhibiting cross sections substantially larger than those used in orthodontic appliances; that is, materials exhibiting a larger cross section than the range of 0.1 mm. to 2.0 mm. As will be appreciated, the preferred orthodontic wires fall within the lower end of the range and conventionally exhibit a cross section of about 0.2 to 1.0 mm. with the preferred wire size typically being about 0.35 to 0.80 mm.

The following examples are given in order that the effectiveness of the present invention may be more fully understood. These examples are set forth for the purpose of illustration only and are not intended in any way to limit the practice of the invention.

EXAMPLE 1

This example is set forth for the purpose of illustrating the variations in the modulus of elasticity and ratio of yield strength to modulus of elasticity for the beta-titanium relative to stainless steel since these factors are a good predictor of the maximum elastic deflection and load deflection rate of an orthodontic appliance.

A standard 18-8 stainless steel orthodontic wire was obtained from Unitek Corporation of Monrovia, Calif. The wire had a diameter of 0.756 mm. (0.030 inches) and was tested for modulus of elasticity and yield strength in its as-received condition.

Mill-processed beta-titanium wire, having a specification composition by weight of 11.5% molybdenum, 6% zirconium and 4.5% tin with the balance being titanium was obtained in the identical diameter size; namely, 0.756 mm. (0.030 inches), in both a solution heat-treated condition and an as-drawn condition. The solution heat-treated material was almost completely beta phase material developed by heating the alloy to 1300–1350° F. and water quenching. The solution heat-treated material was subsequently heated to a temperature of 482° C. (900° F.) for a period of from two to eight hours, and the modulus and strength properties of the material were tested at different time intervals.

The tensile tests were performed with a constant strain rate Instron testing machine using a cross-head rate of 0.5 cm./min. A one-half inch strain gauge extensometer was used with strain magnification of either 400:1 or 1000:1, the extensometer having been slightly modified for the purpose of testing fine wire samples. The extensometer modification is described in the article of A. J. Goldberg et al entitled "Reduction in the Modulus of Elasticity in Orthodontic Wires," *Journal of Dental Research*, Vol. 56, pages 1227–1231, (October 1977).

The stainless steel wire exhibited a yield strength of $23.9 \times 10^4$ psi and a modulus of elasticity of $22.9 \times 10^6$, resulting in a ratio of yield strength to modulus of elasticity of $1.04 \times 10^{-2}$. The as-drawn titanium alloy exhibited a yield strength of $15.1 \times 10^4$ and a modulus of elasticity of $10.1 \times 10^6$ for a ratio of $1.49 \times 10^{-2}$. Both the yield strength and modulus of elasticity of the heat-aged alloy material varied with the time of heat treatment, reaching a maximum value at about four to four and one-half hours. At its maximum ratio value, the material exhibited a yield strength of $19.1 \times 10^4$ and a modulus of elasticity of $13.4 \times 10^6$ for a ratio of $1.42 \times 10^{-2}$. The ratio of the solution heat-treated material varied from $0.97 \times 10^{-2}$ with no heat treatment to the indicated maximum value. An increase in yield strength and modulus upon heating results from the alpha phase precipitation. However, the increase in the ratio of yield strength to modulus results since the modulus of elasticity does not increase at the same rate as the yield strength during this heat aging or alpha-precipitation treatment.

Comparable increases in yield strength and modulus were found when heat aging the same alloy at 1000° F. and 1100° F. The stength rose from a zero treatment level of $10 \times 10^4$ psi to levels of $15.8 \times 10^4$ psi and $15.5 \times 10^4$ psi respectively while the modulus changed from $10 \times 10^6$ psi to $15 \times 10^6$ psi at each temperature level.

EXAMPLE 2

The purpose of this example is to show the correlation between the improved ratio measurements and the maximum elastic deflection properties of the alloy material.

The same materials as in Example 1, but of different wire diameter size, were tested for yield strength and modulus of elasticity. Additionally, the wires were formed into an orthodontic rectangular loop spring having the configuration shown in FIG. 4. The loop had a height of 6 mm., a gingival length of 10 mm. and an interbracket distance of 10 mm. These loop springs were tested for maximum deflection to yield by applying a force at the anterior and posterior bracket position, as indicated by the arrows in FIG. 4. The tests were made using a specially designed spring tester of the type described in the article by D. J. Solonche et al entitled "A Device for Determining the Mechanical Behavior of Orthodontic Appliances", *IEEE Trans on Engineering in Medicine and Biology*, Vol. 24, pages 538–539 (1977). The tester used an LVDT transducer and was capable of detecting permanent deformations after a maximum threshold value had been reached.

The formability of the material was determined using the ADA Specification No. 32 on Orthodontic Wires by cold bending the wire through an angle of 90° over a 1 mm. diameter mandrel to determine the number of bends the wire could withstand prior to fracturing. A 90° bend and a return to the original position was counted as two cold bends. Each test was repeated ten times using various locations on the different wires. The results are set forth in Table I.

The cold bending value for the solution heat treated alloy wire of 0.14 inch diameter without heat aging was 11.14, evidencing its substantially greater ductility and its suitability for use as a ligature wire.

Table I

|  | Stainless Steel** | Alloy (as drawn) | Alloy** (heat aged) |
|---|---|---|---|
| Wire Diameter (in.) | 0.016 | 0.013 | 0.014 |
| Yield Strength @ 0.1% Off Set ($\times 10^4$ psi) | 27.0 | 17.0 | 20.1 |
| Modulus of Elasticity ($\times 10^6$ psi) | 25.1 | 9.4 | 13.8 |
| Ratio of Strength to Modulus ($\times 10^{-2}$) | 1.07 | 1.81 | 1.46 |
| Maximum Deflection to Yield (mm.)*** | 7.5 | 12.0 | 12.0 |
| Force per Unit of Displacement (gm./mm.)*** | 27.2 | 12.7 | 21.2 |
| Cold Bending | 5.1 | 6.2 | 3.8 |

*Stress-relieved for 11 min. @ 400° C.
**Four hours @ 482° C. (900° F.)
***Corrected for different diameters

EXAMPLE 3

The purpose of this example is to show the maximum deflection to yield for another beta-titanium alloy and the effect of heat aging on the deflection.

A standard 18-8 stainless steel orthodontic wire was used as the basis for comparison, the wire having a diameter of 0.025 inches. Mill-processed beta-titanium alloy having the same diameter as the stainless steel was obtained. The alloy had a specification composition by weight of 13% vanadium, 11% chromium and 3% aluminum with the balance being titanium. Each sample was formed into an orthodontic rectangular loop spring, as shown in FIG. 4, having a height of 6 mm., a gingival length of 12 mm. and an interbracket distance of 7 mm. The tests were performed in the manner set forth in Example 2, and the results are set forth in Table II.

TABLE II

| Wire | Heat Treatment Temp. °C. | Time (hr.) | Deflection at Yield (mm.) | Force/Unit of Deflection (gm/mm.) |
|---|---|---|---|---|
| Stainless Steel | — |  | 3.10 | 149.3 |
| Alloy | None |  | 4.50 | 83.3 |
| " | 427 | 5 | 6.10 | 90.8 |
| " | 427 | 9 | 6.50 | 87.5 |
| " | 482 | 0.5 | 5.2 | 91.0 |
| " | 482 | 1.5 | 6.1 | 93.6 |
| " | 538 | 0.5 | 5.25 | 93.1 |
| " | 538 | 3 | 4.7 | 93.6 |

As will be apparent to persons skilled in the art, various modifications, adaptations and variations of the foregoing specific disclosure can be made without departing from the teachings of the present invention.

We claim:

1. In an orthodontic appliance having a force-imparting wire for applying corrective forces to a tooth, said wire having a cross section in the range of about 0.1 mm. to 2.0 mm., the improvement wherein said force-imparting wire is formed from a room temperature stabilized beta-titanium alloy having a modulus of elasticity well below $20 \times 10^6$ psi, said wire having a preselected ratio of yield strength to modulus of elasticity ranging from a level comparable to that of stress relieved 18-8 stainless steel wire of the same cross section up to at least 80% greater than that of such stainless steel wire, whereby said wire is capable of applying a lower and more constant force magnitude with greater accuracy over a longer period thereby enhancing the effective working period of the appliance, said beta-titanium alloy wire having a higher maximum elastic deflection to yield than said stainless steel wire and an ability to withstand extensive bending into complex orthodontic configurations.

2. The orthodontic appliance of claim 1 wherein said beta-titanium alloy has a modulus of elasticity in the range of $8-16 \times 10^6$ psi.

3. The orthodontic appliance of claim 1 wherein said beta-titanium alloy contains a stabilizing amount of a metal selected from the group consisting of molybdenum, columbium, tantalum and vanadium.

4. The orthodontic appliance of claim 1 wherein the deflection to yield of the beta-titanium alloy wire is at least about 50 percent greater than that of 18-8 stainless steel wire.

5. The orthodontic appliance of claim 1 wherein said beta-titanium alloy is hardened by cold working.

6. The orthodontic appliance of claim 1 wherein said beta-titanium alloy is a solution heat treated material that has been heat aged at a temperature above about 400° C.

7. The orthodontic appliance of claim 1 wherein the alloy contains about 11.5 percent by weight molybdenum, 6 percent by weight zirconium and 4.5 percent by weight tin.

8. The orthodontic appliance of claim 1 wherein the alloy contains about 13 percent by weight vanadium, 11 percent by weight chromium and 3 percent by weight aluminum.

9. The orthodontic appliance of claim 1 wherein the alloy contains about 8 percent by weight molybdenum, 8 percent by weight vanadium, 2 percent by weight iron and 3 percent by weight aluminum.

10. A highly ductile orthodontic ligature wire consisting essentially of wire having a cross section in the range of about 0.1 mm. to 2.0 mm. and formed from a room temperature stabilized beta-titanium alloy having a modulus of elasticity well below $20 \times 10^6$ psi, said wire exhibiting a cold bending value as measured by ADA Specification No. 32 at least twice as great as that exhibited by a beta-titanium alloy wire of the same composition and cross section that has been heat aged for four hours at about 482° C.

11. A retaining wire adapted for use in orthodontic clasps and retainers, prosthetic appliances, surgical jaw bars and the like consisting essentially of a wire formed from a room temperature stabilized beta-titanium alloy having a modulus of elasticity well below $20 \times 10^6$ psi, said wire having a preselected ratio of yield strength to modulus of elasticity ranging from a level comparable to that of 18-8 stainless steel wire of the same cross section up to at least 80% greater than that of such stainless steel wire as well as an ability to withstand extensive bending, said wire being capable of applying lower force magnitudes during chewing and having a higher maximum elastic deflection to yield than said stainless steel wire so that retention is enhanced.

* * * * *